United States Patent

Swedlow et al.

[11] Patent Number: 5,368,026
[45] Date of Patent: Nov. 29, 1994

[54] OXIMETER WITH MOTION DETECTION FOR ALARM MODIFICATION

[75] Inventors: David B. Swedlow, Foster City, Calif.; Robert S. Potratz, Lenexa, Kans.

[73] Assignee: Nellcor Incorporated, Pleasanton, Calif.

[21] Appl. No.: 37,953

[22] Filed: Mar. 26, 1993

[51] Int. Cl.$^5$ ............................................. A61B 5/00
[52] U.S. Cl. ............................. 128/633; 364/413.03; 356/41
[58] Field of Search ................ 128/633, 664–667; 356/41; 364/413.03

[56] References Cited

U.S. PATENT DOCUMENTS

| | | |
|---|---|---|
| 4,802,486 | 2/1989 | Goodman et al. |
| 4,824,242 | 4/1989 | Frick et al. ............................ 128/633 |
| 4,859,057 | 8/1989 | Taylor et al. ......................... 128/633 |
| 4,911,167 | 3/1990 | Corenman et al. .................. 128/666 |
| 4,955,379 | 9/1990 | Hall ....................................... 128/633 |
| 4,960,126 | 10/1990 | Conlon et al. ....................... 128/633 |
| 5,025,791 | 6/1991 | Niwa .................................... 128/633 |
| 5,078,136 | 1/1992 | Stone et al. |
| 5,225,672 | 7/1993 | Jones .................................... 128/667 |

*Primary Examiner*—Lee S. Cohen
*Assistant Examiner*—Robert L. Nasser, Jr.
*Attorney, Agent, or Firm*—Townsend and Townsend Khourie and Crew

[57] ABSTRACT

A pulse oximeter which modifies the alarm condition when motion is detected. Basically, if the lack of a pulse is determined to be as a result of motion artifact, the generation of an alarm is postponed. In addition, the display indicates that motion is present and that the last reading is questionable due to the presence of motion. The invention also determines if motion artifact is present from the pulse oximeter detector signal itself. The ratio of the positive and negative peaks of the derivative of the pulse signal are compared to a motion/blood pulse threshold.

19 Claims, 6 Drawing Sheets

OXIMETER WITH MOTION DETECTION FOR ALARM MODIFICATION

BACKGROUND

The present invention relates to a pulse oximeter for detecting blood oxygenation, and in particular to the detection of motion artifact which may affect the detected blood oxygenation signal.

Pulse oximeters typically measure and display various blood flow characteristics including but not limited to blood oxygen saturation of hemoglobin in arterial blood, volume of individual blood pulsations supplying the flesh, and the rate of blood pulsations corresponding to each heartbeat of the patient. The oximeters pass light through human or animal body tissue where blood perfuses the tissue such as a finger, an ear, the nasal septum or the scalp, and photoelectrically sense the absorption of light in the tissue. The amount of light absorbed is then used to calculate the amount of blood constituent being measured.

The light passed through the tissue is selected to be of one or more wavelengths that is absorbed by the blood in an amount representative of the amount of the blood constituent present in the blood. The amount of transmitted light passed through the tissue will vary in accordance with the changing amount of blood constituent in the tissue and the related light absorption.

For example, the Nellcor N-100 oximeter is a microprocessor controlled device that measures oxygen saturation of hemoglobin using light from two light emitting diodes (LED's), one having a discrete frequency of about 660 nanometers in the red light range and the other having a discrete frequency of about 900-920 nanometers in the infrared range. The N-100 oximeter microprocessor uses a four-state clock to provide a bipolar drive current for the two LED's so that a positive current pulse drives the infrared LED and a negative current pulse drives the red LED to illuminate alternately the two LED's so that the incident light will pass through, e.g., a fingertip, and the detected or transmitted light will be detected by a single photodetector. The clock uses a high strobing rate to be easily distinguished from other light sources. The photodetector current changes in response to the red and infrared light transmitted in sequence and is converted to a voltage signal, amplified, and separated by a two-channel synchronous detector—one channel for processing the red light waveform and the other channel for processing the infrared light waveform. The separated signals are filtered to remove the strobing frequency, electrical noise, and ambient noise and then digitized by an analog to digital converter.

The detected digital optical signal is processed by the microprocessor of the N-100 oximeter to analyze and identify optical pulses corresponding to arterial pulses and to develop a history as to pulse periodicity, pulse shape, and determined oxygen saturation. The N-100 oximeter microprocessor decides whether or not to accept a detected pulse as corresponding to an arterial pulse by comparing the detected pulse against the pulse history. To be accepted, a detected pulse must meet certain predetermined criteria, for example, the expected size of the pulse, when the pulse is expected to occur, and the expected ratio of the red light to infrared light of the detected optical pulse in accordance with a desired degree of confidence. Identified individual optical pulses accepted for processing are used to compute the oxygen saturation from the ratio of maximum and minimum pulse levels as seen by the red wavelength compared to the maximum and minimum pulse levels as seen by the infrared wavelength.

The optical signal can be degraded by both noise and motion artifact. One source of noise is ambient light which reaches the light detector. Another source of noise would be electromagnetic coupling from other electronic instruments in the area. Motion of the patient can also affect the signal. For instance, when moving, the coupling between the detector and the skin or the emitter and the skin can be affected, such as by the detector moving away from the skin temporarily, for instance. In addition, since blood is a fluid, it may not move at the same speed as the surrounding tissue, thus resulting in a momentary change in volume at the point the oximeter probe is attached.

Such motion can degrade the signal a doctor is relying on, with the doctor being unaware of it. This is especially true if there is remote monitoring of the patient, the motion is too small to be observed, the doctor is watching the instrument or other parts of the patient, and not the sensor site, or in a fetus, where motion is hidden.

In one oximeter system described in U.S. Pat. No. 5,025,791, an accelerometer is used to detect motion. When motion is detected, readings influenced by motion are either eliminated or indicated as being corrupted. In other systems, such as described in U.S. Pat. No. 4,802,486, assigned to Nellcor, an EKG signal is monitored and correlated to the oximeter reading to provide synchronization to limit the effect of noise and motion artifact pulses on the oximeter readings. This reduces the chances of the oximeter locking on to a periodic motion signal. Still other systems, such as that set forth in U.S. Pat. No. 5,078,136, assigned to Nellcor, use signal processing in an attempt to limit the effect of noise and motion artifact. The '136 patent, for instance, uses linear interpolation and rate of change techniques or selective frequency filtering to analyze the oximeter signal.

Many pulse oximeters have audible alarms which will activate if no pulse signal is detected for a certain period of time, such as 10 seconds. This is clearly desirable to detect when a patient has lost his or her pulse. However, when noise or motion artifact corrupts the pulse signals and prevents the detection of sufficient qualified pulses in a 10 second period, false alarms can be frequently generated and are not only very annoying, but can reduce the confidence in a true alarm situation.

SUMMARY OF THE INVENTION

The present invention provides a pulse oximeter which modifies the alarm condition when motion is detected. Basically, if the lack of a qualified pulse is determined to be as a result of motion artifact, the generation of an alarm is postponed. In addition, the display indicates that motion is present and that the last reading is questionable due to the presence of motion.

In a preferred embodiment, the oximeter operates in three different states. First, in a normal state, qualified pulses are present and processed, and blood oxygen and pulse readings are generated. Second, in a noise state, an alarm time-out period begins to run when there is an absence of sufficient qualified pulses which are not due to motion artifact. Third, a motion state is entered when the lack of sufficient qualified pulses is determined to be due to the presence of motion artifact. This causes the alarm period to be extended.

In a preferred embodiment, when no qualified pulse has been detected for 10 seconds, the oximeter enters a probationary state. A 6.3 second timer is set upon entering the probationary state. 6.3 seconds allows time for 2 heart pulses at 20 beats/min., plus a 5% cushion. If it is determined that the oximeter is in a noise state during this period, an alarm sounds after 6.3 seconds. If, instead, it is determined that motion is present and the oximeter enters the motion state (motion artifact is detected as causing pulses) the alarm generation is extended up to a maximum of 50 seconds. The oximeter can exit the motion state and enter the noise state upon the cessation of the detection of pulses due to the motion artifact, in which case the 6.3 second timer will reset and restart.

Finally, the motion state can be exited and a return to the normal state can occur if a number of clean, qualified pulses are detected. This is preferably the same number of pulses required to be detected upon startup of the oximeter to establish a pulse reading and lock-on to a pulse frequency, but the return criteria may be different from the initial lock-on criteria. Thus, the exiting of the probationary state is made difficult to ensure that a clean pulse signal is indeed present.

The invention also provides a method and apparatus for determining if motion artifact is present from the pulse oximeter detector signal itself. When a pulse is detected, its derivative is calculated. The inventors have observed that a true pulse caused by the bloodflow from a heartbeat has a certain characteristic. That characteristic is that the ratio of the positive peak of the derivative signal to the negative peak of a derivative signal is typically greater than from 1 to 1.4. Motion artifact pulses, on the other hand, have been observed by the inventors to have approximately a 1:1 ratio of the values of the positive peak to the negative peak of the derivative signal. Accordingly, a threshold in the range of 1–1.4 is chosen, with values having a ratio greater than the threshold being considered real pulses, while those lower than the threshold being considered motion artifact pulses.

The present invention provides the advantage of limiting false alarms due to motion while still generating an alarm if motion is present for an extended period.

The present invention also provides the advantage of providing a motion indication by analyzing the existing pulse oximeter detector signal without requiring additional sensors or hardware.

For a fuller understanding of the nature and advantages of the invention, reference should be made to the ensuing detailed description taken in conjunction with the accompanying drawings.

DETAILED DESCRIPTION OF THE PREFERRED EMBODIMENTS

Housing

Figure 1:
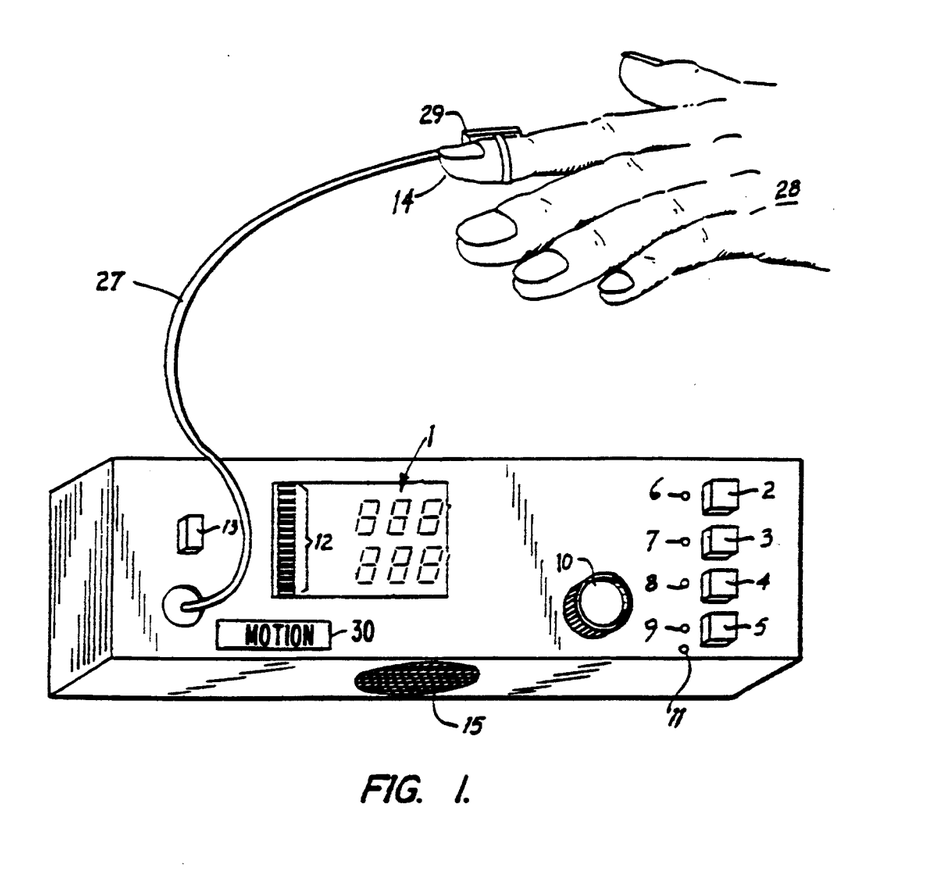
FIG. 1 is a perspective view of a housing for a pulse oximeter according to the present invention.

Referring to FIG. 1, the instrument housing 26 of this invention is illustrated. Outwardly, the housing includes a digit display 1, circuitry select button array 2 through 5, alarm status lights 6 through 9, an optically coupled adjustment knob 10, sync status light 11, LED digital viewmeter 12, and power switch 13. A speaker 15 is placed under and in the instrument housing.

From a connector (not shown) in housing 26 there extend leader wires 27. Wires 27 extend to a detector probe 29. Detector 29 is placed upon the finger 14 of a patient 28. Utilizing the placement of the detector 29 at the finger 14, all of the readings in this invention are made possible.

The oximeter housing also includes a motion indicator 30. When lit up, this indicator shows that motion has been detected. In addition, the digital display 1 will provide a blinking pulse reading with alternating dashes to indicate that the reliability is suspect due to the detection of motion.

Oximeter Circuitry

A description of the electronic circuitry of the Nellcor N-200 pulse oximeter will be first presented, to enable understanding of the present invention. This is only an example of one pulse oximeter in which the present invention may be used.

Figure 2:
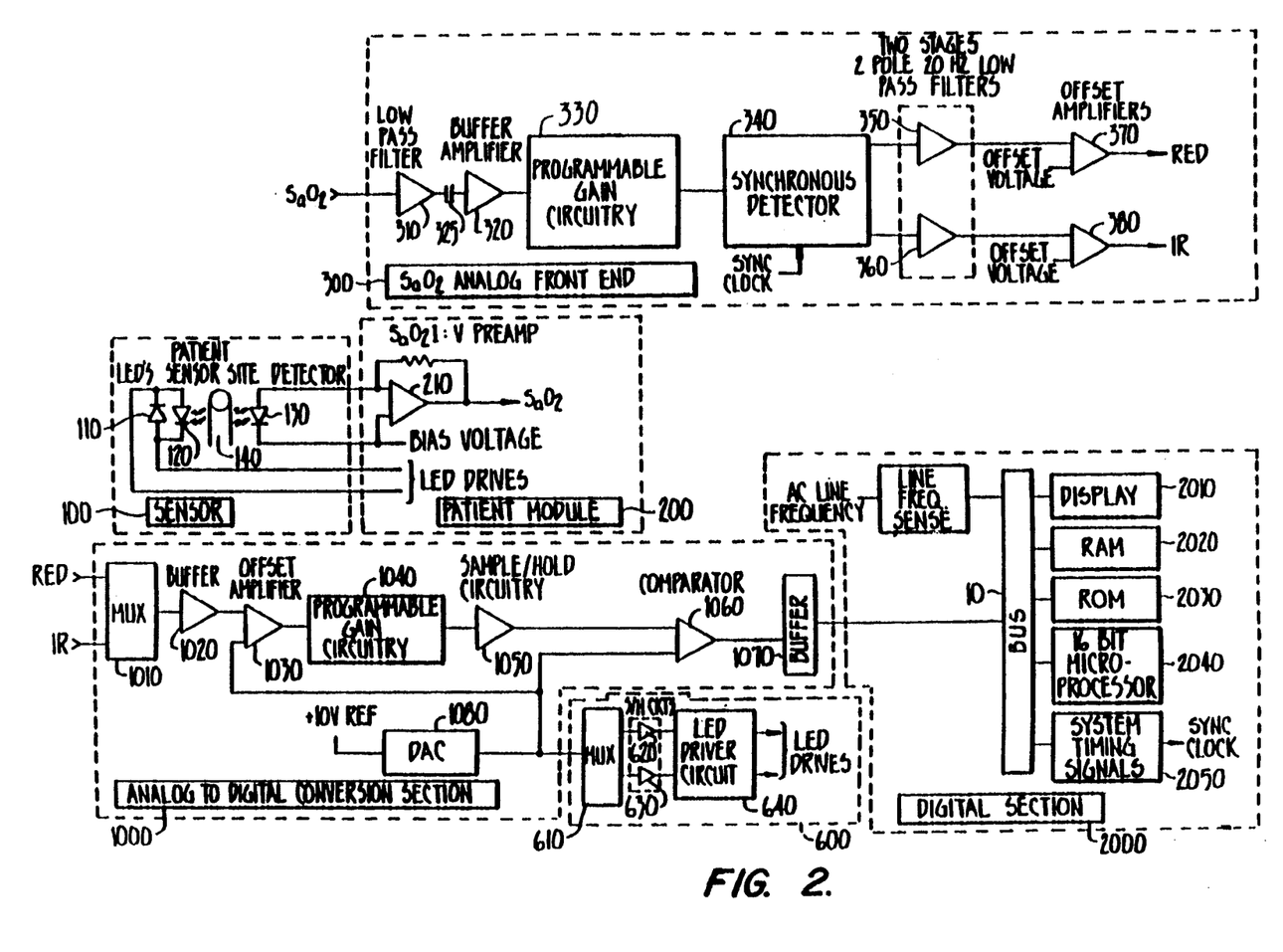
FIG. 2 is a block diagram of the electronic circuitry of the pulse oximeter of FIG. 1.

Referring to FIG. 2, sensor circuit 100 has red LED 110 and infrared LED 120 connected in parallel, anode to cathode, so that the LED drive current alternately illuminates one LED and then the other LED. Circuit 100 also includes photodetector 130, preferably a photodiode, which detects the level of light transmitted through the patient's tissue, e.g., finger 140, as a single, analog optical signal containing both the red and infrared light plethysmographic, detected optical signal waveforms.

Patient module 200 includes preamplifier 210 for preamplifying the analog detected optical signal of photodetector 130. Alternately, the preamplifier may be in the oximeter itself. Preamplifier 210 may be an operational amplifier configured as a current to voltage converter, biased by a positive voltage to extend the dynamic range of the system, thereby converting the photocurrent of photodiode 130 into a usable voltage signal. Patient module 200 also includes leads for passing the LED drive voltages to LEDs 110 and 120.

Saturation analog front end circuit 300 receives the analog optical signal from patient module 200 and filters and processes the detected signal to provide separate red and infrared analog voltage signals corresponding to the detected red and infrared optical pulses. The voltage signal is passed through low pass filter 310 to remove unwanted high frequency components, AC coupled through capacitor 325 to remove the DC component, passed through high pass filter 320 to remove any unwanted low frequencies and passed through buffer 320 and passed through programmable gain stage 330 to amplify and optimize the signal level presented to synchronous detector 340.

Synchronous detector 340 removes any common mode signals present and splits the time multiplexed optical signal into two channels, one representing the red voltage signals and the other representing the infrared voltage signals. Each signal is then passed through respective filter chains having two 2-pole 20 hertz low pass filters 350 and 360, and offset amplifier 370 and 380. The filtered voltage signals now contain the signal information corresponding to the red and infrared detected optical signals.

Analog-to-Digital Converter (ADC) 1000 provides the analog to digital conversions required by the N-200 oximeter. The aforementioned two voltage signals, the red detected optical signal and the infrared detected optical signal from patient module 200, are input to ADC 1000. These signals are conventionally multiplexed and digitized by an expanded range 12-bit analog-to-digital conversion technique, yielding 16-bit resolution. The input signals are passed through multiplexor 1010 and buffer amplifier 1020. The converter stage includes offset amplifier 1030 and programmable gain circuitry 1040 which allows a portion of the signal to be removed and the remainder to be further amplified for greater resolution, sample and hold circuit 1050, comparator 1060, and 12-bit digital to analog convertor 1080. The buffered signal is passed through offset amplifier 1030 to add a DC bias to the signal wherein a portion of the signal is removed and the balance is amplified by being passed through programmable gain circuitry 1040 to improve the resolution. The amplified signal is then passed through sample and hold circuit 1050, the output of which is fed to one input of comparator 1060. The other input of comparator 1060 is the output of digital to analog (DAC) converter 1080 so that when the inputs to comparator 1060 are the same, the analog voltage at the sample and hold circuit is given the corresponding digital word in DAC converter 1080 which is then stored in an appropriate memory device as the digitized data for the sample and the next sample is sent to sample and hold circuit 1050 to be digitized.

DAC 1080 also generates the sensor LED drive voltages, under the control of microprocessor 2040, using analog multiplexor 610, which separates the incoming analog signal into one of two channels for respectively driving the red and infrared LEDs, having respective sample and hold circuits 620 and 630, and LED driver circuit 640 for converting the respective analog voltage signals into the respective positive and negative bipolar current signals for driving LEDs 110 and 120.

Digital Signal Processor (DSP) 2000 controls all aspects of the signal processing operation including the signal input and output and intermediate processing. The apparatus includes 16-bit microprocessor 2040 and its associated support circuitry including data bus 10, random access memory (RAM) 2020, read only memory (ROM) 2030, a conventional LED display device 2020 (not described in detail), and system timing circuit 2050 for providing the necessary clock synchronizing signals.

Interrupt programs control the collection and digitization of incoming optical signal data. As particular events occur, various software flags are raised which transfer operation to various routines that are called from a main loop processing routine.

Probationary Period

Figure 3:
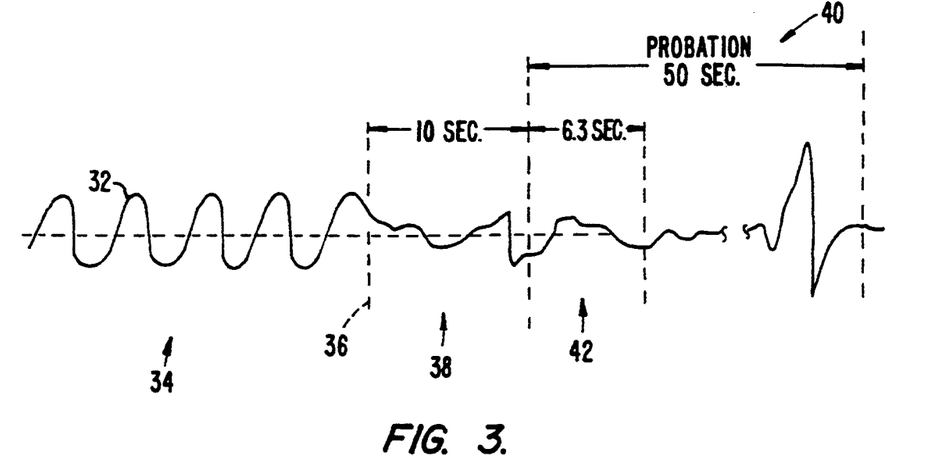
FIG. 3 is a timing diagram illustrating the probationary period of the present invention.

FIG. 3 illustrates a pulse oximeter detector signal 32 with bloodflow pulses being regularly detected in a first period 34. At a time 36, no more qualified pulses are detected. This can be due to noise, motion artifact, or the absence of a blood pulse. The oximeter will continue looking for qualified pulses for a 10 second period 38 after the last qualified pulse. If no qualified pulse is detected within this time, a probationary state 40 is entered. In the first portion of the probationary state, a 6.3 second timer is set for a period 42.

State Diagram

Figure 4:
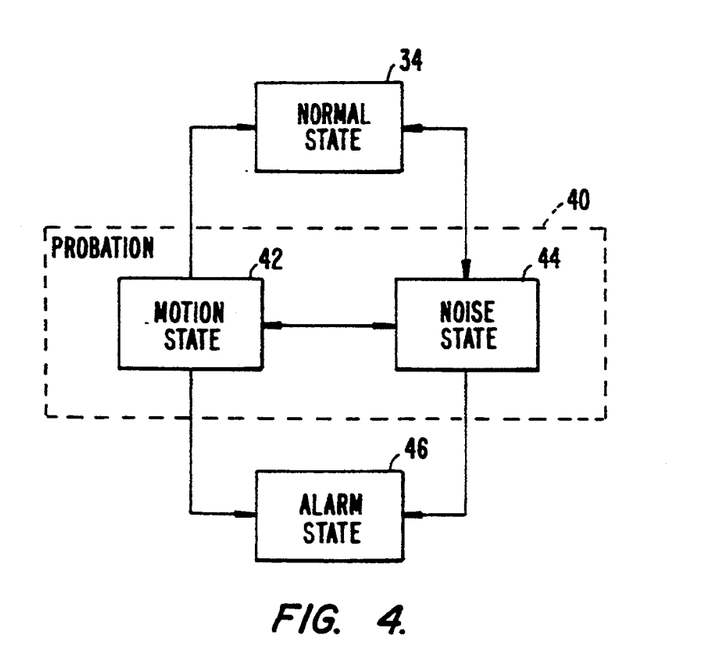
FIG. 4 is a state diagram illustrating the normal, motion and noise state of the present invention.

Referring to FIG. 4 as well, probationary state 40 is indicated in the state diagram of FIG. 4 as including a motion state 42 and a noise state 44. When the 6.3 second timer is set, this is initially the noise state 44. The noise state preferrably has affirmative criteria, but can also simply be the absence of motion or a qualified signal. An example of an affirmative criteria is the lack of correlation between the IR and red channels for a pulse. In the preferred embodiment, at least 2 pulses (noise or otherwise) must be detected as noise in the 6.3 second period. If no pulse is detected for 3.1 seconds, the preceding 3.1 second period is presumed to be a pulse, and is analyzed accordingly.

If motion is detected, motion state 42 is entered and the 6.3 second timer is halted. This can continue for the maximum probation period of 50 seconds. If motion continues to be detected after 50 seconds, an alarm is generated upon alarm state 46 of FIG. 4 being entered. The alarm will also be generated when the 6.3 second timer runs out.

Flow chart of Probationary Period Operation

Figure 5:
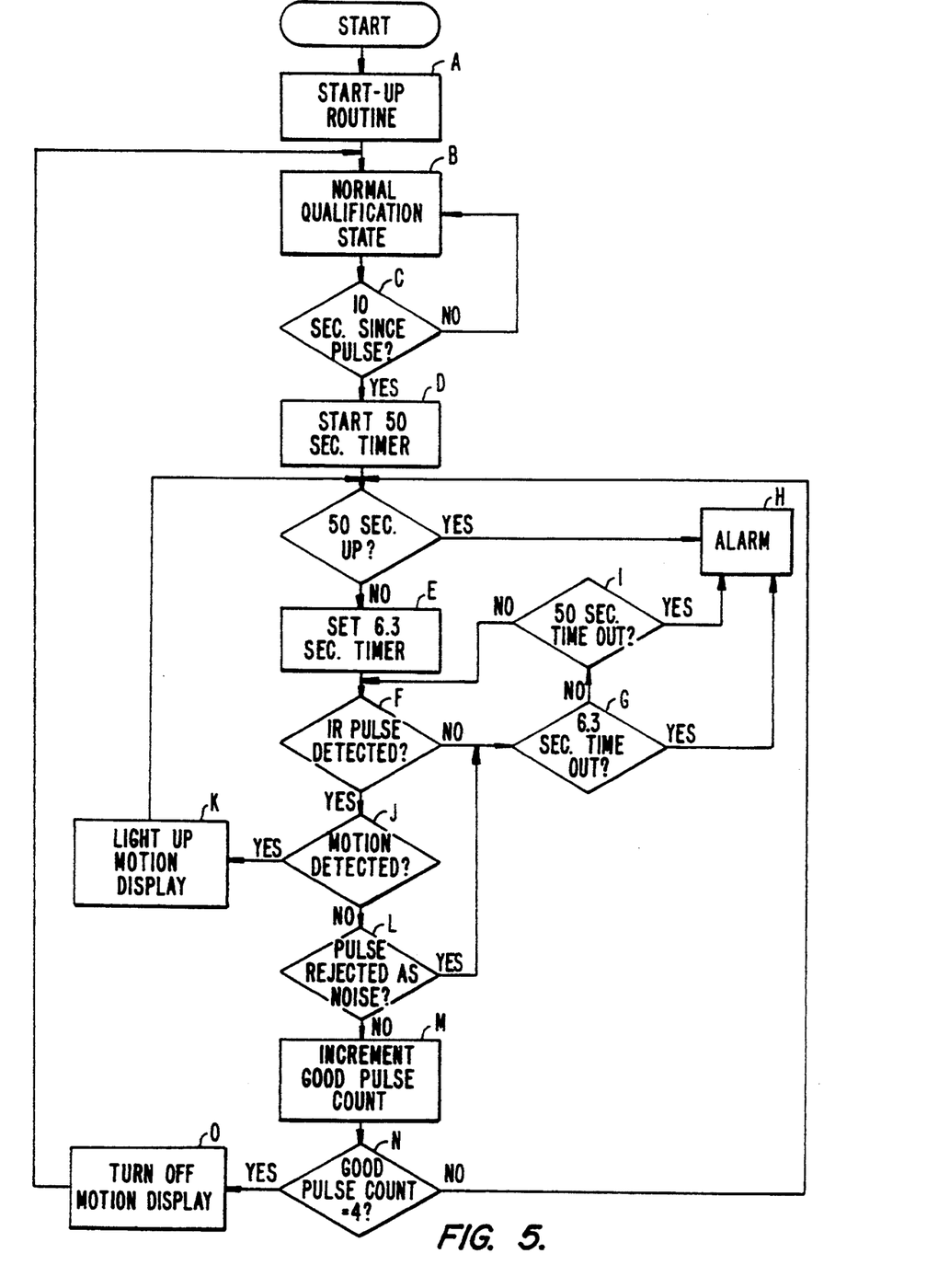
FIG. 5 is a flowchart illustrating the operation of the present invention.

FIG. 5 is a flowchart illustrating the software used to implement the states of FIG. 4. This software would reside in RAM 2020 of FIG. 2. After the start, a startup routine (step A) is entered wherein pulses are qualified and a good pulse signal is indicated after four consecutive qualified pulses. The qualification is done according to well-known techniques. Once this startup is completed, the software enters a normal qualification state (step B).

After each pulse is detected, a 10 second timer is started (step C). If 10 seconds has passed since the last qualified pulse was detected, the system enters the probation state and a 50 second timer is set (step D). The 6.3 second timer is also set (step E). The signal is then monitored for the detection of an IR (infrared) pulse (step F). The IR channel is monitored because the IR tends to be a lower noise source than the red signal. If no qualified pulse is detected for 6.3 seconds (step G) the alarm is sounded (step H). The 50 second timer is also checked (step I) in case it expires before a particular 6.3 second period.

If an IR pulse is detected in the probation period, a test is then done to see if motion is detected (step J). The detection of motion is shown in more detail in the motion detection flowchart of FIG. 6. Upon the detection of motion, the motion display on the monitor is illuminated (step K), and the 6.3 second timer is reset (step E) and the system continues to monitor for another pulse. If a pulse is detected and there is no motion, a test is done to determine if it should be rejected as being noisy (step L). In the noise state, a slower averaging algorithm is used than in the normal qualified state to insure that a false indication of a good blood pulse is not generated. If there is no noise rejection, it is a qualified pulse, and a qualified pulse count is incremented (step M). Upon the count equalling four consecutive pulses (step N), the probationary period is exited after turning off the display (step O).

Motion Detection

The motion detection can be from a separate signal, motion sensor, such as an accelerometer or piezoelectric device attached to the oximeter sensor. Preferably, however, motion detection is accomplished by analyzing the optical detector signal itself.

Figure 6:
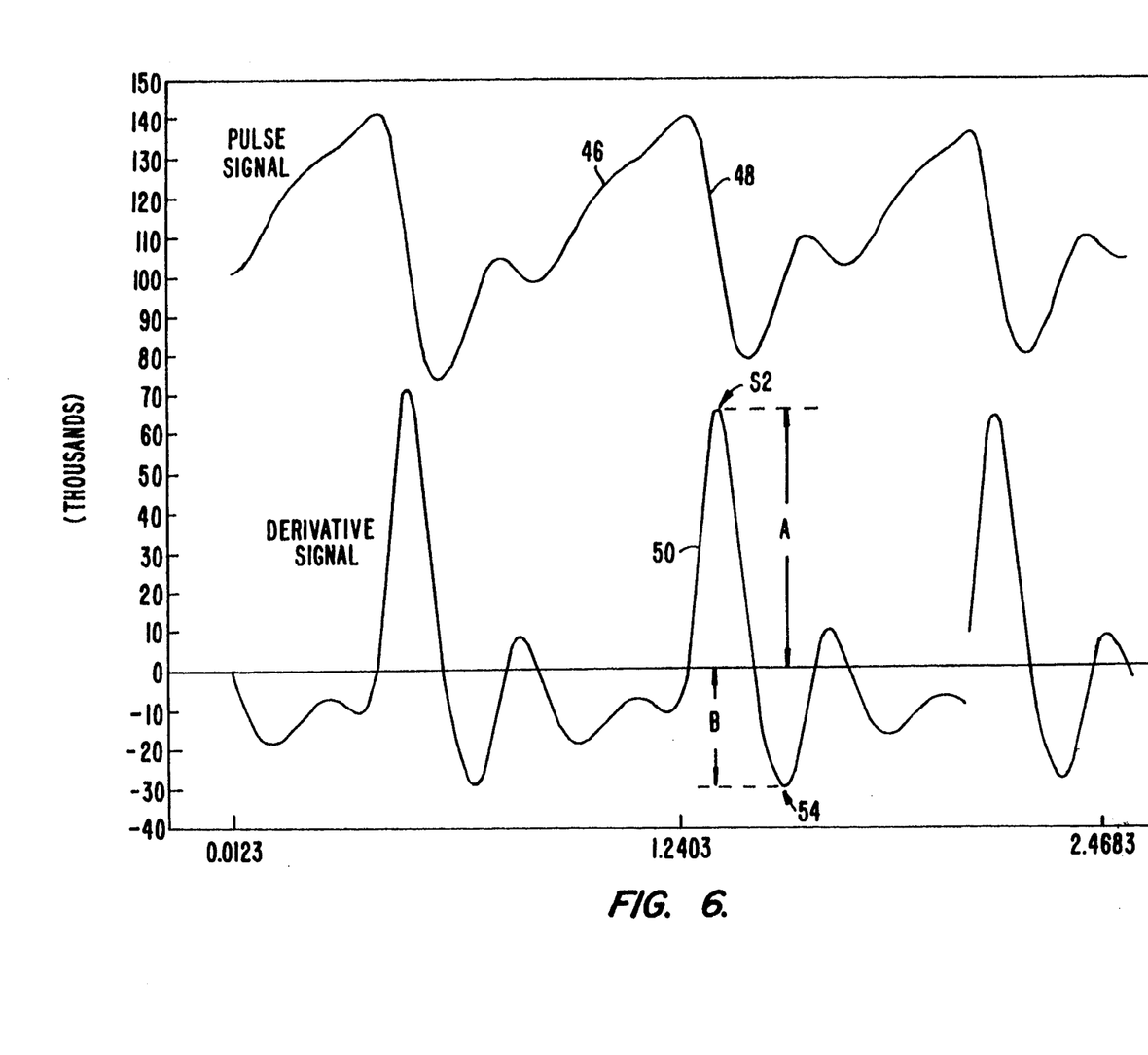
FIG. 6 is a diagram of a typical blood pulse signal and its derivative.

FIG. 6 illustrates a typical qualified blood pulse. The pulse has a rising side 46, and then, after peaking, has a slowly trailing side 48. The derivative of this signal is calculated in microprocessor 2040 of FIG. 2 of the pulse oximeter. A plot of the derivative is also shown in FIG. 6 for the blood pulse. The derivative has a rising portion 50 corresponding to portion 46 of the pulse. After the peak of the pulse, the derivative of the signal rapidly progresses from a positive peak 52 to a negative peak 54, and then slowly approaches zero again. The height of the positive peak of the derivative signal, A, and the height of the negative peak, B, have been observed to have an A/B ratio of greater than 1–1.4 for a typical blood pulse. Motion artifact, on the other hand, typically has a 1/1 ratio.

Accordingly, the oximeter of the present invention, after determining the derivative of the pulse signal, calculates the ratio of A/B and compares it to a threshold to indicate whether it is a blood pulse signal or a motion signal pulse. Preferably, the threshold is in a range of 1.0–1.4. In a preferred embodiment, a ratio of 260/256 is used, which equals 1.0196/1. The selection of the exact threshold is tradeoff between rejecting good pulses and rejecting motion. A ratio of 1.4 has been observed to reject approximately 95% of motion artifact, but may also reject some good pulses as well. The ratio of 1.0196 provides a conservative level to retain most qualified pulses, will giving a good level of rejection of motion artifact.

Figure 7:
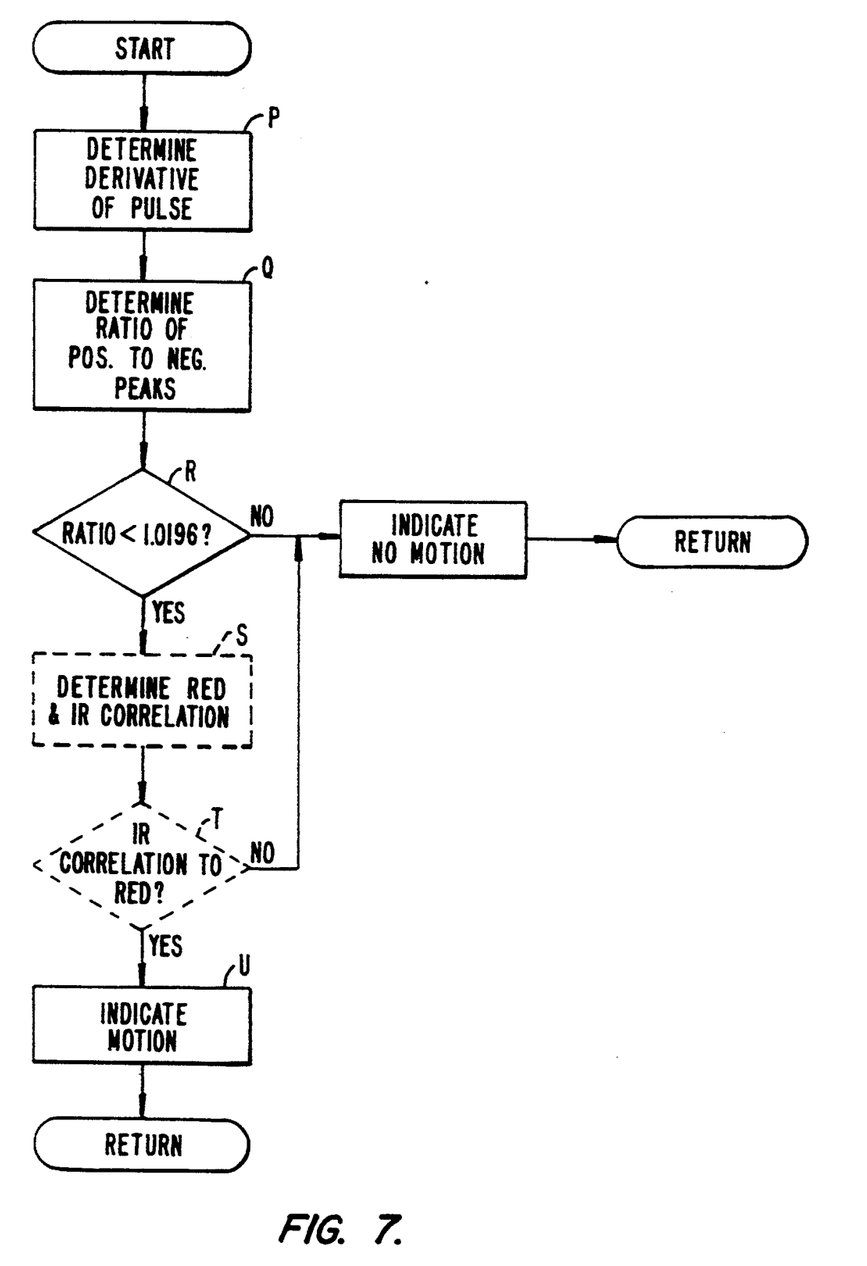
FIG. 7 is a subroutine flowchart illustrating the motion detection test of FIG. 5.

FIG. 7 is a flowchart for the software routine for determining if a pulse is due to motion. When the routine is called, it first determines the derivative of the pulse signal (step P). Next, the ratio A/B of the positive to negative peak of the derivative signal is determined (step Q). If the ratio is less than 1.0196/1 (step R), the signal is presumably a motion pulse. If it is greater, it is an indication that the pulse is not motion (either qualified or noise pulse) (step S) and there is a return from the subroutine.

An optional second or alternative motion test may be used in addition to or in place of the ratio test. It has been observed by the inventors that for a motion signal, there will be correlation of the pulses in the infrared and red channels. Noise, on the other hand, tends to be uncorrelated, with different values in the IR and red channels. The correlation of the IR and red pulses are thus determined (optional step S) and compared (optional step T), and if they are not correlated, the pulse is presumably noise, and there is a return from the subroutine. If the infrared and red pulses are correlated, this is an indication that the pulse is due to motion, and a motion flag is set (step U), and there is a return from the subroutine.

Alternately, a different motion test could be used. For instance, the saturation value of a pulse could be determined using the ratio of ratios, as is well known in the industry. This calculation can be done for several different parts of the pulse. For a qualified blood pulse, the values should be approximately the same. If the values differ, it could be motion or noise. The correlation test could then be run to determine if it is noise or motion.

As will be understood by those familiar with the art, the present invention may be embodied in other specific forms without departing from the spirit or essential characteristics thereof. For example, only a single one of the motion tests of FIG. 8 could be used, or the use of a piezoelectric accelerometer sensor could be substituted for the optical signal analysis in order to determine whether a motion signal is present. Accordingly, the disclosure of the preferred embodiment of the invention is intended to be illustrative, without limiting the scope of the invention which is set forth in the following claims.

What is claimed is:

1. A pulse oximeter comprising:
   means for emitting light;
   sensor means for producing a detector signal corresponding to absorption of said light emitted by blood constituents;
   means for determining oxygen saturation based on the detector signal;
   control means, coupled to said sensor means, for qualifying pulses in the detector signal corresponding to arterial pulses;
   alarm generating means for generating an alarm when no qualified pulses are detected in a predetermined time-out period;
   motion artifact means for determining whether motion artifact is present during said time-out period; and
   means, responsive to said motion artifact means, for modifying the timing of the generation of said alarm.

2. The pulse oximeter of claim 1 wherein said means for modifying includes a state machine having:
   means for operating in a qualified signal state for detecting and analyzing qualified pulses;
   means for operating in a probationary state for both determining whether non-qualified pulses are due to noise or motion artifact and searching for qualified pulses, said motion artifact means being activated during said probationary state;
   means for transitioning from said qualified signal state to said probationary state when no qualified pulses are detected for a first period of time; and
   means for transitioning from said probationary state to said qualified signal state when a predetermined number of qualified signals are detected in said probationary state.

3. The pulse oximeter of claim 2 wherein said state machine is a programmed microprocessor.

4. The pulse oximeter of claim 2 wherein said probationary state includes:
   means for operating in a motion artifact state wherein motion artifact is detected and said time-out period is extended; and
   means for operating in a noise state wherein no motion artifact is detected and said time-out period is not extended.

5. The pulse oximeter of claim 2 further comprising means for activating said alarm if said probationary state extends for more than a maximum probation period of time.

6. The pulse oximeter of claim 1 wherein said motion artifact means comprises:
   means for detecting a pulse waveform in said detected signal;

means for determining the derivative of said pulse waveform;

means for determining the ratio of a positive peak of said derivative to a negative peak of said derivative;

means for comparing said ratio to a threshold value; and means for indicating motion artifact when said ratio is less than said threshold.

7. The pulse oximeter of claim 6 wherein said means for comparing is programmed with said threshold being between 1 and 1.4.

8. The pulse oximeter of claim 1 wherein said means for emitting includes means for producing an infrared (IR) signal and a red signal, said motion artifact means comprising:

means for correlating an IR pulse to a corresponding red pulse; and means for indicating motion artifact when said pulse is not qualified and said IR and red pulses are correlated.

9. The apparatus of claim 1 further comprising:

means, coupled to said control means, for calculating a numerical pulse rate from said pulses;

a display, coupled to said means for calculating, for indicating said numerical pulse rate;

means, responsive to said motion artifact means and coupled to said display, for alternating said numerical pulse rate with dashes when motion artifact is present.

10. An apparatus for detecting motion artifact in a pulse oximeter signal comprising:

means for emitting light at a body;

means for receiving light from said body to generate said pulse oximeter signal;

means for detecting a pulse waveform in said pulse oximeter signal;

means for determining the derivative of said pulse waveform;

means for determining the ratio of a positive peak of said derivative to a negative peak of said derivative;

means for comparing said ratio to a threshold value; and means for indicating motion artifact when said ratio is less than said threshold.

11. A method of operating a pulse oximeter comprising the steps of:

emitting light;

producing a detector signal corresponding to absorption of said emitted light by blood constituents;

determining oxygen saturation based on the detector signal;

qualifying pulses in the detector signal corresponding to arterial pulses;

generating an alarm when no qualified pulses are detected in a predetermined time-out period;

determining whether motion artifact is present during said time-out period; and modifying the timing of the generation of said alarm based on whether motion artifact is present.

12. The method of claim 11 wherein said modifying step includes operating in a qualified signal state for detecting and analyzing qualified pulses, and operating in a probationary state for both determining whether non-qualified pulses are due to noise or motion artifact and searching for qualified pulses, said step of determining whether motion artifact is present being performed during said probationary state;

and further comprising the steps of:

transitioning from said qualified signal state to said probationary state when no qualified pulses are detected for a first period of time; and transitioning from said probationary state to said qualified signal state when a predetermined number of qualified signals are detected in said probationary state.

13. The method of claim 12 further comprising the step of performing said steps of operating and transitioning in a software program.

14. The method of claim 12 wherein said probationary state includes:

a motion artifact state wherein motion artifact is detected and said time-out period is extended; and a noise state wherein no motion artifact is detected and said time-out period is not extended.

15. The method of claim 12 further comprising the step of activating said alarm if said probationary state extends for more that a maximum probation period of time.

16. The method of claim 10 wherein said determining step comprises the steps of:

detecting a pulse waveform in said detected signal;

determining the derivative of said pulse waveform;

determining the ratio of a positive peak of said derivative to a negative peak of said derivative;

comparing said ratio to a threshold value; and indicating motion artifact when said ratio is less than said threshold.

17. The method of claim 16 wherein said threshold is between 1 and 1.4.

18. The method of claim 10 wherein said step of emitting includes producing an infrared (IR) signal and a red signal, said determining step comprising the steps of:

correlating an IR pulse to a corresponding red pulse; and indicating motion artifact when said pulse is not qualified and said IR and red pulses are correlated.

19. A method for detecting motion artifact in a pulse oximeter signal comprising the steps of:

emitting light at a body;

receiving light from said body to generate said pulse oximeter signal;

detecting a pulse waveform in said pulse oximeter signal;

determining the derivative of said pulse waveform;

determining the ratio of a positive peak of said derivative to a negative peak of said derivative;

comparing said ratio to a threshold value; and indicating motion artifact when said ratio is less than said threshold.

* * * * *